(12) United States Patent
Ryotokuji (10) Patent No.: US 9,370,620 B2
(45) Date of Patent: Jun. 21, 2016

(54) DRUG SUPPLY START TIMING DETERMINATION METHOD AND DRUG CONVEYANCE SYSTEM

(76) Inventor: Kenji Ryotokuji, Chiba (JP)

( * ) Notice: Subject to any disclaimer, the term of this patent is extended or adjusted under 35 U.S.C. 154(b) by 195 days.

(21) Appl. No.: 14/240,250

(22) PCT Filed: Aug. 13, 2012

(86) PCT No.: PCT/JP2012/070945
§ 371 (c)(1),
(2), (4) Date: Feb. 21, 2014

(87) PCT Pub. No.: WO2013/027688
PCT Pub. Date: Feb. 28, 2013

(65) Prior Publication Data
US 2014/0200544 A1    Jul. 17, 2014

(30) Foreign Application Priority Data

Aug. 22, 2011  (JP) .................. 2011-180704
Nov. 22, 2011  (JP) .................. 2011-254617

(51) Int. Cl.
| | | |
|---|---|---|
| *A61M 5/172* | (2006.01) | |
| *A61B 5/00* | (2006.01) | |
| *A61B 5/026* | (2006.01) | |
| *A61H 39/08* | (2006.01) | |
| *A61N 7/00* | (2006.01) | |

(Continued)

(52) U.S. Cl.
CPC ............ *A61M 5/1723* (2013.01); *A61B 5/0261* (2013.01); *A61B 5/4839* (2013.01); *A61B 5/01* (2013.01); *A61B 5/4836* (2013.01); *A61F 7/007* (2013.01); *A61F 2007/0093* (2013.01); *A61F 2007/0096* (2013.01); *A61H 39/086* (2013.01); *A61H 2201/105* (2013.01); *A61H 2205/125* (2013.01); *A61H 2230/25* (2013.01); *A61N 7/00* (2013.01)

(58) Field of Classification Search
CPC . A61M 5/1723; A61B 5/4836; A61B 5/4839; A61B 5/4848; A61B 5/4884; A61B 5/026; A61B 5/0261; A61H 39/086; A61H 2201/105; A61H 2205/125; A61H 2230/25; A61H 2230/255; A61F 7/007
See application file for complete search history.

(56) References Cited

U.S. PATENT DOCUMENTS 5,860,957 A * 1/1999 Jacobsen .................. A61N 1/30
                                                        604/140
5,930,635 A * 7/1999 Bashir .................. H01L 21/8228
                                                        257/E21.611

(Continued)

FOREIGN PATENT DOCUMENTS

| JP | 2004-123638 A | 4/2004 |
| JP | 2010-540409 A | 12/2010 |

OTHER PUBLICATIONS

International Search Report dated Nov. 20, 2012 issued in correponding application No. PCT/JP2012/070945.

*Primary Examiner* — Andrew Gilbert
(74) *Attorney, Agent, or Firm* — Westerman, Hattori, Daniels & Adrian, LLP (57) ABSTRACT

The present invention relates to a method for determining start timing of supply of drug to be given in which a peripheral circulatory function and an autonomic nervous function are activated through a stimulus applied to a stimulus application origin part of a body surface by an acupuncture needle or warm heating etc., and a drug conveyance system according to the method for determining start timing of supply of drug.

4 Claims, 7 Drawing Sheets

(51) Int. Cl.
*A61B 5/01* (2006.01)
*A61F 7/00* (2006.01)

(56) References Cited

U.S. PATENT DOCUMENTS

| | | | | |
|---|---|---|---|---|
| 6,058,331 A * | 5/2000 | King | A61N 1/3605 | |
| | | | 607/2 | |
| 2004/0147996 A1 * | 7/2004 | Miazga | A61N 1/0551 | |
| | | | 607/142 | |
| 2006/0195168 A1 * | 8/2006 | Dunbar | A61F 7/007 | |
| | | | 607/108 | |
| 2007/0225614 A1 * | 9/2007 | Naghavi | A61B 5/01 | |
| | | | 600/549 | |
| 2008/0255453 A1 * | 10/2008 | Matsunaga | A61B 5/021 | |
| | | | 600/445 | |
| 2008/0279896 A1 | 11/2008 | Heinen et al. | | |
| 2013/0041396 A1 * | 2/2013 | Ryotokuji | A61H 39/04 | |
| | | | 606/189 | |
| 2016/0034782 A1 * | 2/2016 | Nakano | G06K 9/6215 | |
| | | | 382/118 | |

\* cited by examiner

DRUG SUPPLY START TIMING DETERMINATION METHOD AND DRUG CONVEYANCE SYSTEM

TECHNICAL FIELD

The present invention relates to a method for determining start timing of supply of drug to be given in a state where a peripheral circulatory function and an autonomic nervous function are activated through a stimulus to a stimulus application origin part of a body surface by an acupuncture needles or heating etc., and a drug conveyance system based on the method for determining start timing of supply of drug.

BACKGROUND ART

The nervous system of a human body consists of a somatic nerve system and an autonomic nervous system. The autonomic nervous system is further divided into a sympathetic system and a subsympathetic system. The sympathetic nervous system reacts at a stress period. A stimulus to the sympathetic nerves increases a cardiac beat rate and blood pressure, and suppresses generation of secretion in glands etc. On the contrary, parasympathetic nerves reduce the cardiac beat rate and blood pressure, and stimulates secretion of a gland. The sympathetic nervous system is activated while receiving stress.

A physical reaction to the stress is suppressed by the active hypothalamus-pituitary-adrenal axis which discharges stress hormone containing cortisol. If a mental stress is accumulated daily, stress-related gastric and duodenal ulcer etc. will occur.

Many ways such as a measurement of amylase in saliva, a measurement of catecholamines and cortisol in serum, and a measurement of the catecholamines in urine, etc. are known in order to determine sympathetic nervous tone as an indication of a stress level of a person.

In this way, mechanism due to vasodilatation and influence on the sympathetic nerve, which are caused by stimulating a part of a body surface of a human body with heat, acupuncture, etc., have been considered. In such an action in which the blood vessel dilates, it is considered that production of calcitonin gene related peptide increases by the stimulus. It is considered that a discharge of CGRP etc. is enhanced due to an increase in a muscle blood flow by stimulating the nerves etc. That is, it is considered that this is done by mechanism in which an axon-reflex mechanism arises by the stimulus to afferent nerves etc., and the CGRP is discharged from ends so that blood vessels of a controlled area dilate.

In this way, conventionally, it is pointed out that a stimulus to specific part of a human body by acupuncture or warm temperature is performed, whereby it is possible to improve lifestyle-related diseases, such as diabetes, obesity, and high blood pressure. However, the effects by the stimulus were not fully satisfactory for patients.

SUMMARY OF INVENTION

Technical Problem

The present inventor found out a method for efficiently administering a drug in order to improve lifestyle-related diseases, such as diabetes, obesity, and high blood pressure. The present inventor found out that when a stimulus is given by an acupuncture needle or warm temperature heating to specific stimulus application origin part of a body surface, the blood flow volume increases before and after the stimulus is given. And based on the standpoint in which the blood flow volume increases by giving the stimulus by the acupuncture needle or warm temperature heating to this stimulus application origin part of a body surface, when a drug supply timing is determined by regarding an increase rate of the blood flow volume after a stimulus to that before the stimulus as an index of a drug supply start timing, the drug supply timing can be efficiently determined, so that the drug can be supplied to a patient at an optimal stage.

Furthermore, it is an object of the present invention to determine a drug supply timing by regarding an increase rate of a blood flow volume by a stimulus as an index of a drug supply start timing, and supply a drug based on the determined timing so that it is possible to efficiently convey the drug inside the body thereby reducing a dose of the drug whereby a big effect of the drug can be expected. It is preferable that supply of the drug may be achieved by sticking or applying the drug on the stimulus application origin part, in addition to supplying it from a mouth.

Here, the increase rate of blood flow volume means an increase rate of the blood flow volume after giving a stimulus to the blood flow volume before giving the stimulus thereto, in case where the blood flow volume after giving the stimulus and the blood flow volume before giving the stimulus are measured. And it is preferable to continuously supply the drug after an improvement in the increase rate of the blood flow volume is shown.

Furthermore, according to the present invention, the stimulus application origin parts of the body surface are found where parasympathetic nerve dominance is maintained by the stimulus given by an acupuncture needle or warm temperature heating, and long-term sthenic status of sympathetic nerves can be improved. Since these stimulus application origin parts are found, it is though that great contribution to efficient drug administration can be made.

That is, according to the present invention, the stimulus application origin parts by an acupuncture needle or warm temperature heating is considered as the origin of a stimulus, and it is desirable to determine a drug supply timing by regarding an increase rate of blood flow volume after stimulus application to that before the stimulus, as an index of a drug supply start timing, and to supply the drug to the inside of the body after that.

According to the present invention, while an increase in the blood flow volume is observed by a stimulus in the stimulus application origin part(s) of a body surface, they are parts where it is possible to achieve medical effects, such as normalization of the blood pressure resulting from stress, successive diminution of stress, an increase in body temperature, a gradual decrease of neutral fat and cholesterol, an improvement of a blood sugar level by relief of insulin resistance.

Solution to Problem

A drug supply start timing determination method according to the present invention, comprises a step of applying a stimulus to a stimulus application origin part of a body surface with a stimulus applying apparatus, a step of measuring a blood flow volume by a laser Doppler tissue rheometer which is attached to an inner and central part of a wrist joint, and a step of determining a drug supply timing by regarding an increase in the blood flow volume after application of a stimulus to that before the stimulus, as an index of a drug supply start timing.

The drug supply timing is at time when the increase rate of blood flow volume is 60% or greater, preferably 100% or greater.

The stimulus application origin part is in foot sole of right and/or left at least one of part of os metatarsale primam 1 and 2 interossous; a part of os metatarsale primam 2 and 3 interossous; and a part that intersects the perpendicular line of the medial malleolus on an extension line of the medial margin on os metatarsale primam 1 and 2 interossous.

The stimulus application origin part is a thyroid part.

The stimulus application origin part is a part between an outer skin crust and crease side of inner side boundary part of the head of proximal phalanx and the base of 1st proximal phalanx of left and/or right foot.

It is desirable to apply the stimuli to at least two stimulus application origin parts non-simultaneously and independently.

It is desirable that the stimulus be one selected from an acupuncture needle stimulus, a warm temperature heating stimulus, a photic stimulus, magnetic stimulus, and an ultrasonic stimulus.

The warm temperature heating stimulus apparatus is equipped with a guide element for thermal stimulus which is made up of two kinds of different metals.

The acupuncture needle is equipped with an indwelling member detained inside a part.

A drug is accommodated inside the indwelling member and the drug is released.

The drug conveyance system continuously supplies the drug after the drug supply start timing is determined.

The drug conveyance system continuously supplies a drug, thereby getting rid of stress.

The drug is released from drug accommodated inside the indwelling member provided in the acupuncture needle.

The drug, which is applied to or stuck on the part, is released by heat from the drug.

The drug is conveyed by the drug conveyance system.

Advantageous Effects of Invention

As the blood flow volume increases in the part to which stimulus is applied by warm temperature heating, the following are achieved: a rise in core body temperature, a fall of systolic blood pressure, an increase in salivary amylase, a decrease in cortisol, an improvement of a liver function, a decrease in total cholesterol, a decrease in good and bad cholesterols, a decrease in blood sugar level, a decrease in A.I. (arteriosclerosis index), an increase in an adiponectin, and a decrease in leptin. As a result of measuring the balance of autonomic nerves by a heartrater, the stress resistance increases.

DESCRIPTION OF EMBODIMENT

Mechanism due to vasodilatation and mechanism due to influence on sympathetic nerves, which are caused by stimulating a stimulus application origin part, are considered. An action, in which this blood vessel dilates, is considered to increase production of calcitonin gene related peptide (CGRP) by applying a stimulus.

It is considered as mechanism in which an increase in a muscle blood flow due to the stimulus to nerves etc. accelerates the discharge of CGRP etc. That is, it is considered as mechanism in which the stimulus to afferent nerves etc. causes an axon-reflex mechanism thereby, and the CGRP is discharged from ends thereof, so that blood vessels of a controlled area dilate.

Furthermore, an influence on autonomic nerve activity which governs blood vessels is also assumed. Blood vessels of, for example, muscles, are governed by the adrenergic sympathetic nerves and cholinergic sympathetic nerves. The former is vasoconstrictor carried out through an α receptor and the latter is vasodilator carried out through acetylcholine. The former always works for the blood vessels of muscles at time of a rest and at time of tonus, and always maintains the blood vessels in a contraction state. On the other hand, it is considered that the latter increases blood flow volume by loosening the smooth muscle of blood vessels in response to acetylcholine discharged from the nerve endings.

When the stimulus by an acupuncture needle or warm temperature heating maintains parasympathetic nerve dominance, long-term sthenic status of sympathetic nerves is improved, and further, from a viewpoint of a rise in core body temperature, a blood pressure change, etc. it is thought that the stimulus of an acupuncture needle, warm temperature heating, etc. adjusts a blood flow of each organ through systemic blood pressure and the autonomic nerves.

The mechanism and influence on sympathetic nerves become remarkable, because of an increase of the blood flow volume caused by a vasodilatation due to the stimulus to the stimulus application origin part of a body surface, so that the stimulus application origin part in the present invention, are preferably parts where there are effects, such as normalization of the blood pressure resulting from stress, a gradual decrease of stress, elevation of body temperature, a gradual decrease of neutral fat and cholesterol, an improvement of the blood sugar level due to relief of insulin resistance etc.

The blood flow volume obtained by giving a stimulus to this stimulus application origin part is measured, and the blood flow volume obtained before giving the stimulus thereto is measured, and a drug supply timing is determined by considering an increase rate of blood flow volume before and after the stimulus application, as an index of a drug supply start timing.

As for the measurement, it is desirable to measure the blood flow volume by a laser Doppler tissue rheometer which is attached to an inner and central part of a wrist joint. A laser Doppler tissue rheometer ALF21D (manufactured by Adovans), converts light reflected from a tissue when irradiating the living tissue with semiconductor laser light (wavelength of 780 nm), into an electrical signal, and processes it, thereby obtaining blood flow information on the living tissue. A change of the blood flow volume at time of a 15 minute rest after application of the stimulus was measured by using this laser tissue rheometer ALF21D wherein a C type laser probe (10 mm in diameter, 3 mm in thickness, a laser irradiation area of 2 mm, and 1 mm in measurement depth), was attached to a center of a wrist joint striation of a healthy adult.

The laser tissue blood flow volume measurement is based on principle in which Doppler shift (frequency change) which is produced when laser light collides with red blood cells flowing through the inside of a blood vessel, and receives scattering thereof, is used. This measuring method is characterized in non-invasiveness, immediate responsiveness and possibility of continuous measurement. Furthermore, in ALF21D, which was used this time, display of blood flow volume in ml/min/100 g unit is possible, and this is because signal processing based on the theory of Bonner et al.[4)] is performed.

It is desirable that determination of a drug supply start timing be made after the blood flow volume before applying a stimulus and the blood flow volume after applying the stimulus are measured by the laser Doppler tissue rheometer so that an increase in blood flow volume is observed. That is, a drug supply timing is preferably time when the increase rate becomes so that the blood flow is 60% or greater, preferably 100% or greater than that at time when it is observed.

The mechanism, in which blood flow volume is increased by giving a stimulus to a stimulus application origin part(s), will be give below. Mental stress to a live body stimulates sympathetic nerves through a cerebral limbic system and a hypothalamic pituitary so that blood vessels are contracted, whereby microcirculation including the viscus of the live body is lowered. When the stimulus to the predetermined part of a body surface is applied in the case of the lowering reaction of the blood flow, a significant rise in body temperature of peripheral at 3 mm and 5 mm under skin, and suppression of secretion of stress hormones; ACTH and cortisol, are observed.

Furthermore, vasoactive intestinal peptide (VIP), which is a bioactive hormone, is secreted from an alimentary tract, a pancreas, and a hypothalamic area, and increases a bowel peristalsis thereby increasing blood flow including the alimentary tract. Furthermore, vascularization and blood vessel permeability of microvessels are increased by a vascular endothelial cell growth factor (VEGF). Since these VIP and VEGF significantly increase by a stimulus to a specific part, it is thought that a viscus blood flow and a peripheral blood flow are increased by causing both actions of VIP and VEGF.

From these results, it is considered that while a sympathetic activity and an overresponse of tropic hormones of hypothalamic pituitary, through automatic nerves, due to a stimulus to a live body acts on a hypothalamic area and suppresses a discharge of stress hormones, a blood flow is increased through the VIP and VEGF.

As to the increase in blood flow volume, it is considered that the speed of the blood flow volume through a sympathetic flow response (SFR) by stress decreases, and stress hormones are suppressed so that the blood flow increases through VIP and VEGF.

The stimulus application origin parts of a body surface to which a stimulus is applied, are not limited to those described in Examples 1 through 3, as long as they are parts from which it is possible to obtain an increase in blood flow volume by a stimulus, and to obtain a medical beneficial result by the stimulus. The parts described in Example 1 are especially preferable as the stimulus application origin parts of a body surface to which a stimulus is given.

The stimulus application origin part is in foot sole of right and/or left at least one of at least one of part of os metatarsale primam 1 and 2 interossous; a part of os metatarsale primam 2 and 3 interossous; and a part that intersects the perpendicular line of the medial malleolus on an extension line of the medial margin on os metatarsale primam 1 and 2 interossous.

In addition, the stimulus application origin part is a thyroid part. The stimulus application origin part is a part between an outer skin crust and crease side of inner side boundary part of the head of proximal phalanx and the base of 1st proximal phalanx of left and/or right foot.

It is desirable to apply the stimuli to at least two stimulus application origin parts non-simultaneously and independently.

Although it is desirable that the stimuli are applied thereto by an electrical type warm temperature apparatus, it is not limited to warm temperature stimulus, and an acupuncture needle stimulus, moxibustion stimulus, and moreover a photic stimulus, magnetic stimulus, and an ultrasonic stimulus and low frequency stimulus may be used.

Figure 1:
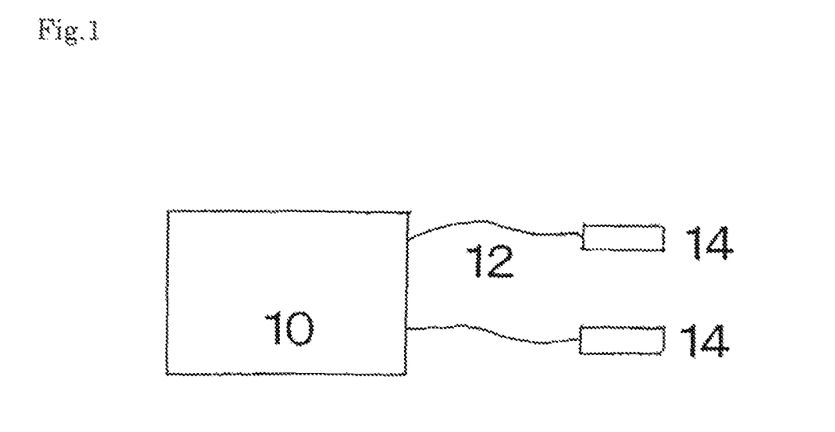
FIG. 1 is a schematic view showing an electrical type warm temperature apparatus used for the present invention.
Figure 2:
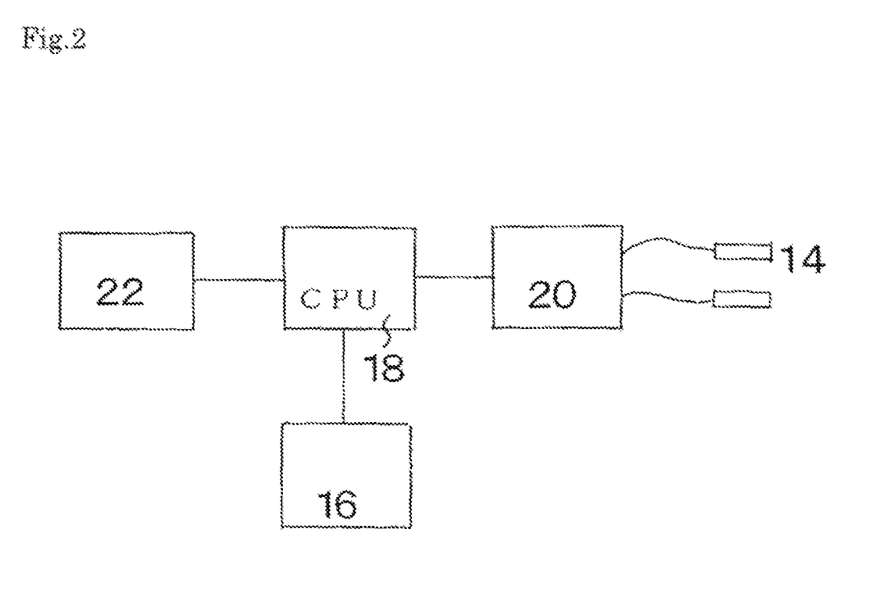
FIG. 2 is a schematic view of a circuit diagram of electrical type warm temperature apparatus.

FIG. 1 is a schematic view showing an electrical type warm temperature heating apparatus used for the present invention. FIG. 2 is a schematic view of a circuit diagram of the electrical type warm temperature heating apparatus.

The electrical type warm temperature heating apparatus is equipped with a main body 10 of the apparatus, in which a control function is built, and guide elements 14 for a thermal stimulus, which are connected with the main body 10 of the apparatus by conducting wires 12. The main body 10 of the apparatus has a memory unit 16 for memorizing thermal stimulus patterns, a control unit (CPU) 18 which reads out a thermal stimulus pattern from the memory unit 16, and an output unit 20 for supplying the thermal stimulus pattern to the guide elements 14 for the thermal stimulus. The thermal stimulus is applied to the above-mentioned parts according to the thermal stimulus pattern.

The control unit (CPU) 18 is connected to the memory unit 16. Thermal stimulus waveforms for obtaining a stimulus condition equivalent to that obtained from combustion of moxa, are stored in the memory unit 16. The control unit (CPU) 18 reads out a thermal stimulus waveform from the memory unit 16, controls an output to heating elements based on detection of a temperature sensor 22, and outputs the thermal stimulus pattern to the guide elements for a thermal stimulus.

The main body 10 of the apparatus is connected to two or more guide elements for a thermal stimulus in order to supply the thermal stimulus pattern to the above-mentioned at least two different parts. In this manner, the selected thermal stimulus waveform is applied to the parts of a body surface, through the guide elements for a thermal stimulus.

As to the guide elements for a thermal stimulus, heat conduction boards of the guide elements for a thermal stimulus, which are placed on two parts, are made up of at least two kinds of different metals. Aluminum and steel are used therefor in this embodiment.

The temperature sensor is provided at a predetermined position of a housing in contact with part of a human body, detects the temperature at the position, and gives a detection signal to a sensor amplifier. The control unit (CPU) controls an output of an electric power generating circuit so that the temperature of that in contact with the cutaneous surface of a human body does not exceed a predetermined temperature. The warm temperature heating apparatus controls the surface temperature of the guide elements for a thermal stimulus at 40° C. to 50° C.±5° C.

When the heating temperature of the heating elements, which is detected by the temperature sensor, is lower than or equal to a desired reference temperature, a positive side period of a pulse signal is controlled so as to be long and a negative side period to be short according to the output of the temperature sensor, and in addition, in a state at the reference temperature, conversely a positive side period is controlled so as to be short and negative side period to be long.

Figure 3:
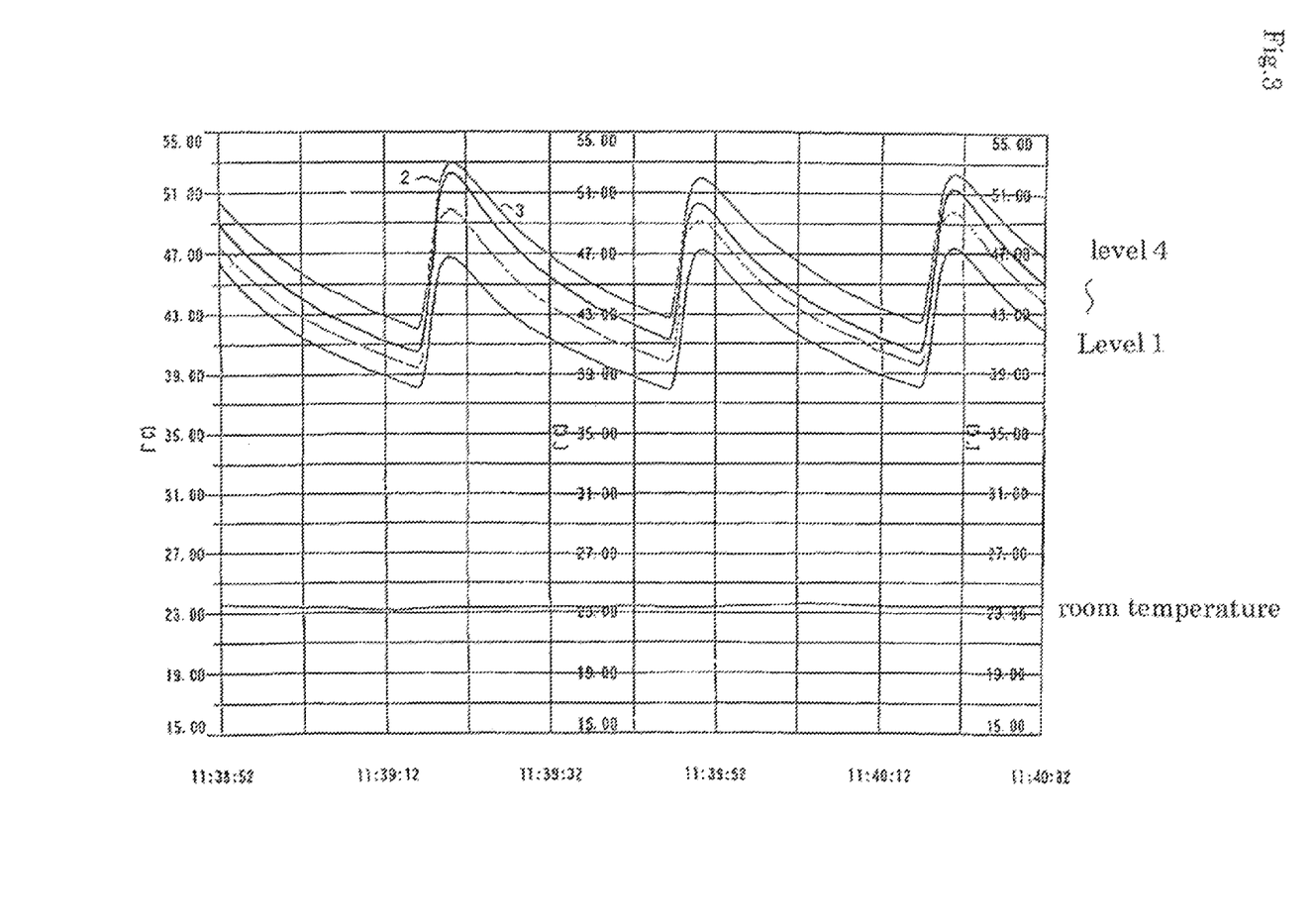
FIG. 3 is a schematic view showing a thermal stimulus wave form obtained by controlling an electrical type warm temperature apparatus.

FIG. 3 show a desirable thermal stimulus waveform obtained by controlling the above-mentioned electrical type warm temperature heating apparatus. The thermal stimulus waveforms 8 includes a heating waveform 2 obtained by raising the temperature by heating to a predetermined peak temperature of 50±5° C., and a heat dissipation waveform 3 which is formed by turning off heating after reaching the peak temperature. It is desirable that the heating waveform 2 is a convex type heating waveform 2 obtained by raising the temperature by heating to a predetermined peak temperature of 50±5° C., an upward sloping line shape heating waveform or a concave type heating waveform. Furthermore, the heating waveform may be not only the above-mentioned heating waveform but may be saw-tooth waveform or a convexo-concave shape waveform.

One cycle of a thermal stimulus waveform includes a thermal stimulus waveform which consists of a warming waveform and a heat dissipation waveform, and an interval to the next warming curve. One cycle of a thermal-stimulus pattern is desirably set so that the thermal stimulus region is from 1 second to 30 seconds and the interval between these heating regions is from 1 second to 10 seconds. A thermal stimulus pattern includes independent thermal stimulus waveforms, which are not substantially overlapped with each other and which are phase-shifted from each other. And a cycle of the thermal stimulus pattern is desirably repeated for from 10 minutes for 30 minutes.

Figure 4:
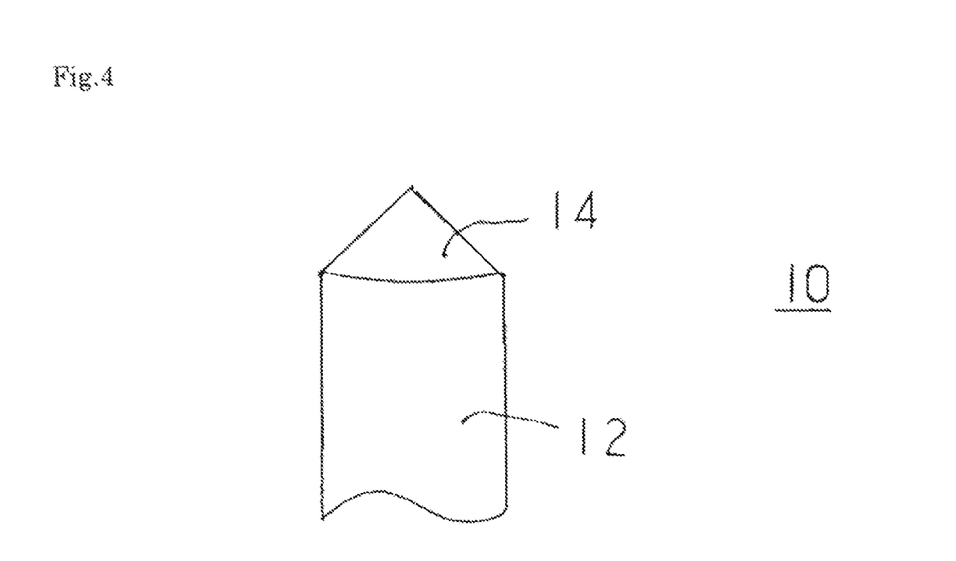
FIG. 4 shows a schematic view showing a part impact giving means.

FIG. 4 shows a schematic view of a part impact giving means which acts as an acupuncture needle. The part impact giving means 10 is equipped with an indwelling member 14 attached at the tip thereof, and a support fine line 12 which is attached to the indwelling member 14 by using a fitting means 22. The support fine line is from 15 mm-90 mm in length, and 0.1 mm in diameter. It is made from 3 mm stainless steel. The indwelling member has a sphenoidal head portion which is made of gold and which is 1 mm in length. After the indwelling member is inserted in a part, the fine line and the indwelling member are separated from each other and the indwelling member is placed in the part. The fitting means 22, by which the indwelling member and the support fine line are fit to each other at a position where the indwelling member is in the part in the body, has a curve shape. In addition, the part impact giving means 10 is from 15 mm-90 mm in length, and 0.1 mm in diameter. This may be made from a 3 mm support fine line made of stainless steel.

A human body part is stuck by the support fine line, and the indwelling member is placed in the part, and heat is given to the support fine line from a heat source, and the indwelling member is separated from the support fine line by using a difference between the thermal expansion coefficient of the material of the indwelling member and that of the support fine line, so that the indwelling member is made to detain in the part. In addition, it is desirable to incline the support fine line toward a detention position by 30 degrees to 60 degrees so as to stick in the part.

Moreover, the support fine line may be provided in the tip side of a pressing device, and the indwelling member is disposed in the support fine line, wherein the detain member is pressed by piston of the pressing device so as to be detained in the part.

The indwelling member has an engaging means for engaging the indwelling member with the body part so as not to flow from the indwelling position in the body part, not to rotate and not come out. The engaging means has an angle portion formed in the indwelling member, wherein the shape thereof is, for example, circular, convexo-concave, angled or triangular. Moreover, the indwelling member itself may be formed in a sphenoidal shape, a triangular pyramid, an elliptical cone, or a polygonal pyramid.

Figure 5:
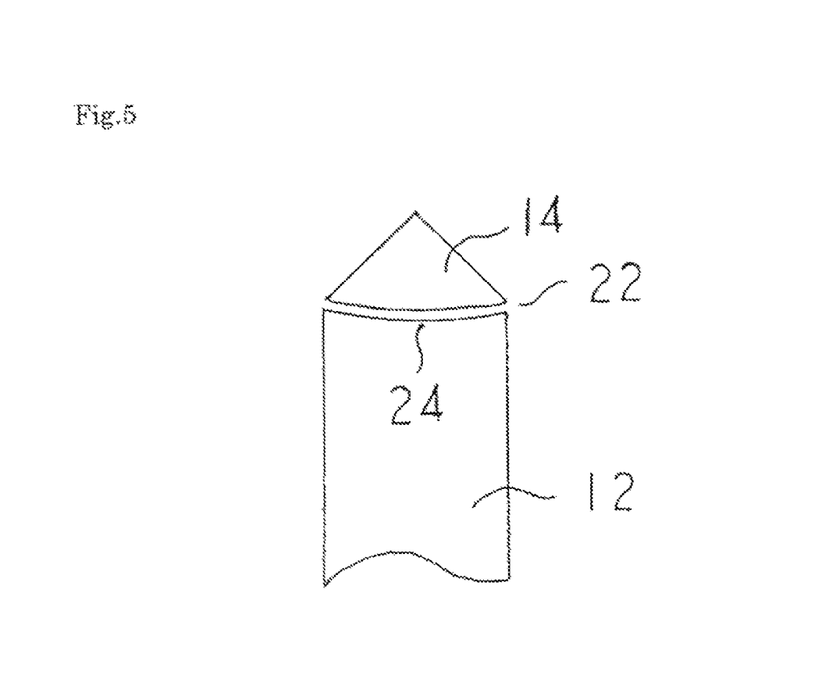
FIG. 5 is a schematic view showing an indwelling member and an insertion member of a support fine line.
Figure 6:
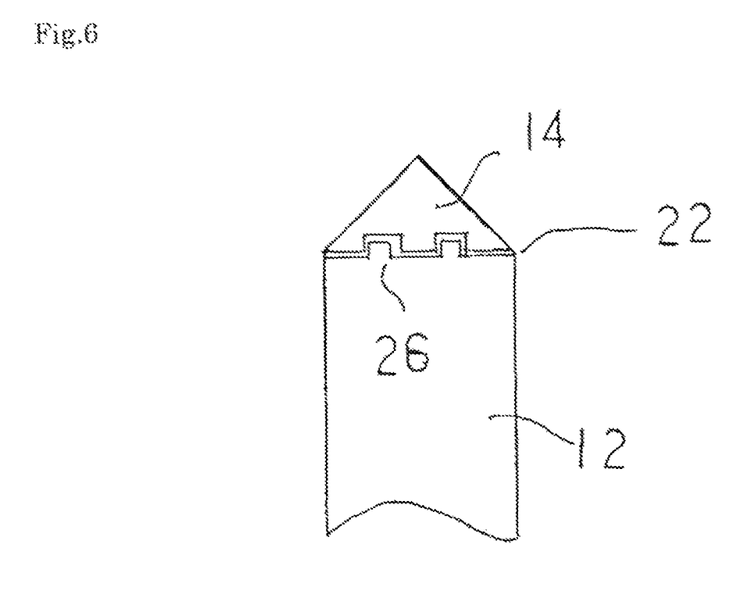
FIG. 6 is a schematic view showing another indwelling member and another insertion member of a support fine line.
Figure 7:
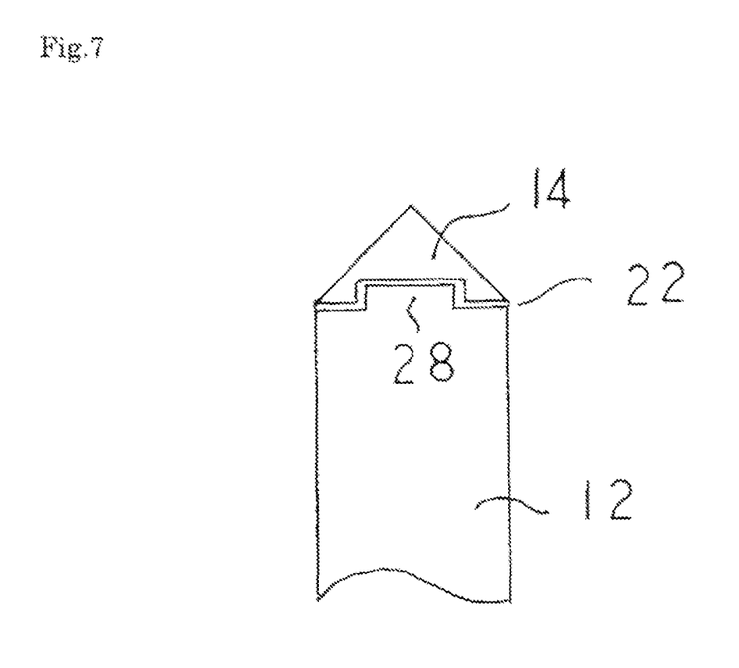
FIG. 7 is a schematic view showing another indwelling member and another insertion member of a support fine line.
Figure 8:
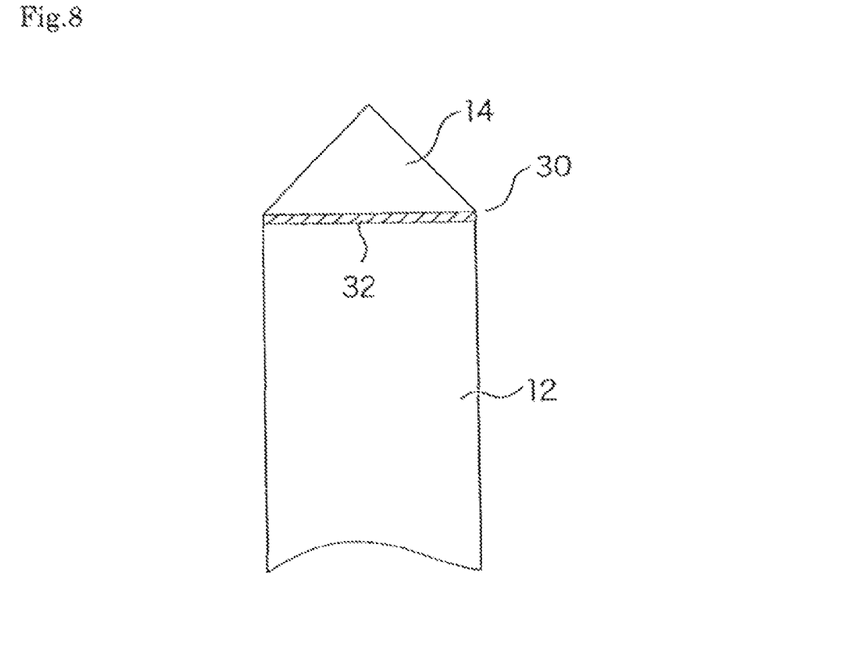
FIG. 8 is a schematic view showing another fitting means for an indwelling member and a support fine line.

FIG. 5 to FIG. 8 are schematic views, each showing a fitting means 22 for fitting the indwelling member and the support fine line. FIG. 5 is a schematic view showing a state where the indwelling member 14 and the support fine line 12 are fit in each other by a fitting means 22 in which a surface of the support fine line 12 facing the indwelling member 14 forms the concave portion 24. FIG. 6 is a schematic view showing a state where the indwelling member 14 and the support fine line 12 are fit in each other by a fitting means 22, in which a surface of the support fine line 12 facing the indwelling member 14, forms a concavo-convex portion 26. FIG. 7 is a schematic view showing a state where the indwelling member 14 and the support fine line 12 are fit in each other by a fitting means 22, in which a surface of the support fine line 12 facing the indwelling member 14 forms a concave portion 28. Furthermore, FIG. 8 is a schematic diagram showing a state where a surface of the support fine line 12 facing the indwelling member 14 serves as a connecting face 30, and an adhesive agent 32 is applied to the connecting face. Glue is used for the adhesive agent.

The indwelling member and the support fine line are provided by the fitting means, and the fitting state of the fitting means for the indwelling member and the support fine line is released and both are separated from each other when heat is conducted from the support fine line to the indwelling member according to a difference in thermal expansion coefficient. It is desirable that the fitting means for the indwelling member and the support fine line forms a curve, convexo-concave, or concave portion for using the difference in thermal expansion coefficient. In a state where heat is not conducted to the indwelling member and the support fine line, both do not come off from each other and are integrally formed, and if the heat from a heat source is given to the support fine line so that the heat is conducted to the indwelling member through the support fine line, a gap is formed in the fitting faces according to the difference between the thermal expansion coefficient of the indwelling member and that of the support fine line, whereby both can be separated and come off from each other.

Moreover, an adhesive agent may be applied to the connecting portion, and the indwelling member and the support fine line may be separated and disconnected from each other. An adhesive agent may be applied to the connecting portion where the indwelling member and the support fine line are fit in each other. The connecting face may have a curve, convexo-concave, or concave portion. Although various materials can be used as the adhesive agent, a material, which is harmless to a human body, is desirable. For example, they are glue, an epoxy resin based material, etc. The indwelling member and the support fine line may screw together, thereby joining together.

Figure 9:
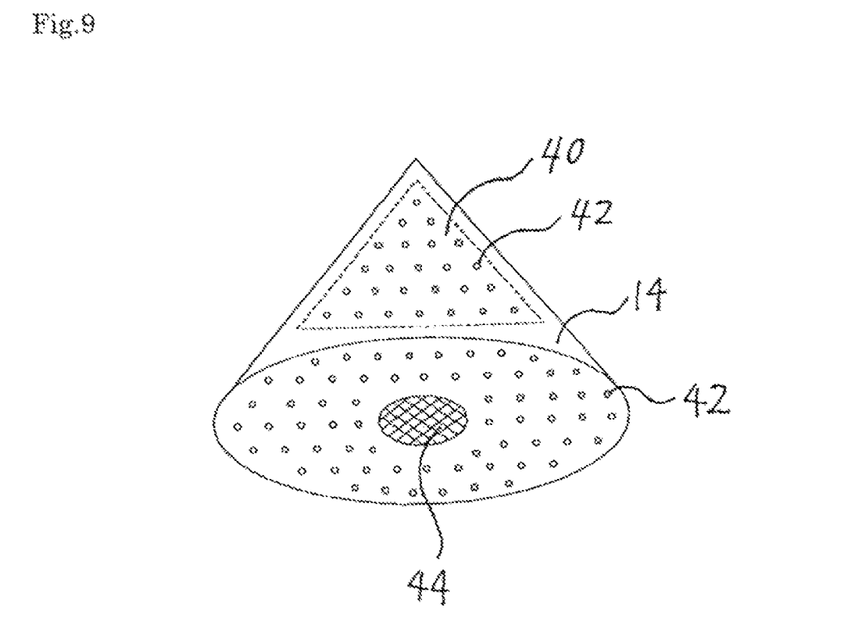
FIG. 9 is a schematic view showing a drug releasing means from an indwelling member.

When a drug 40 is put in the inside of the indwelling member 14, and the drug is released and applied at the above-mentioned parts such as thyroid gland, it is desirable to have a releasing means so that a drug may be released in the inside of the body from the indwelling member. As shown in FIG. 9, it is considered that, as a releasing means, in case where the indwelling member is made of metal such as gold, the indwelling member is formed as a porous body by forming a plurality of fine pores 42 therein; an admixture in which detention material and a drug are mixed with each other is formed; the indwelling member itself is gradually dissolves; or a drug in the inside is discharged etc. Moreover, in order to periodically add a drug to the inside of the indwelling member by a syringe etc., it is desirable to provide a hole etc. for filling the drug. For example, in part of the fitting portion of the metal fine line with the indwelling member, a net member 44 is provided in the indwelling member. By providing the knitted body, it becomes possible to suitably pour the drug through the knitted body with an injection needle.

The stimulus application origin part used for determining a chug supply timing by considering an increase rate of a blood flow volume before and after the above-mentioned stimulus as an index of a drug supply start timing, will be explained in Examples. The stimulus application origin parts are parts where it is possible to achieve medical effects such as an increase in blood flow volume by the stimulus, normalization of the blood pressure resulting from stress by the stimulus, successive diminution of stress, an increase in body temperature, a gradual decrease of neutral fat and cholesterol, an improvement of a blood sugar level by relief of insulin resistance.

It is desirable that the stimuli to the stimulus application origin parts are non-simultaneously and independently applied to at least two of the stimulus application origin parts, that is, in foot sole of right and/or left of at least one of part of os metatarsale primam 1 and 2 interossous; a part of os metatarsale primam 2 and 3 interossous; and a part that intersects the perpendicular line of the medial malleolus on an extension line of the medial margin on os metatarsale primam 1 and 2 interossous; a thyroid part; and is a part between an outer skin crust and crease side of inner side boundary part of the head of proximal phalanx and the base of 1st proximal phalanx of left and/or right foot.

Example 1

Figure 10:
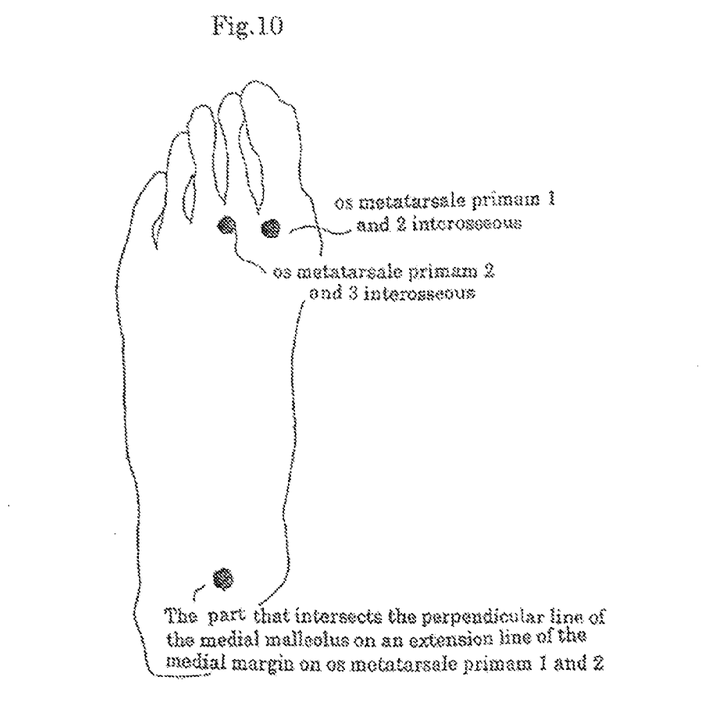
FIG. 10 is a schematic view showing a stimulus part of a sole.

The stimulus application origin part is at least one of the stimulus application origin parts: in foot sole of right and/or left of at least one of part of os metatarsale primam 1 and 2 interossous; a part of os metatarsale primam 2 and 3 interossous; and a part that intersects the perpendicular line of the medial malleolus on an extension line of the medial margin on os metatarsale primam 1 and 2 interossous (Refer to FIG. 10).

Subjects therefore were adult men and women. An electric type warm temperature heating apparatus MXA-8000 (SO-257) was used for applying a warm temperature heating stimulus to the above-mentioned stimulus parts. A probe thereof is 10 mm in diameter, and a heating stimulus of warm temperature whose peak is 50±5° C. was set and performed for 15 minutes. The probe was attached to the following warm temperature heating stimulus parts of a body surface, and the warm temperature heating stimulus was performed at temperature of 40° C. to 50° C.

The warm temperature heating stimulus was non-simultaneously and independently given to the parts. The above-mentioned thermal stimulus pattern was applied thereto as the thermal stimulus.

Taking into consideration influences on the psychological stress through autonomic nerves, the subjects were kept at rest in a state of a dorsal position for 20 minutes. After that, the blood pressure, core body temperature, salivary amylase, and HEARTRATER (artery age) were measured before a stimulus. Then, a warm temperature stimulus was performed for 15 minutes, and then they are measured again immediately after the stimulus.

Figure 11:
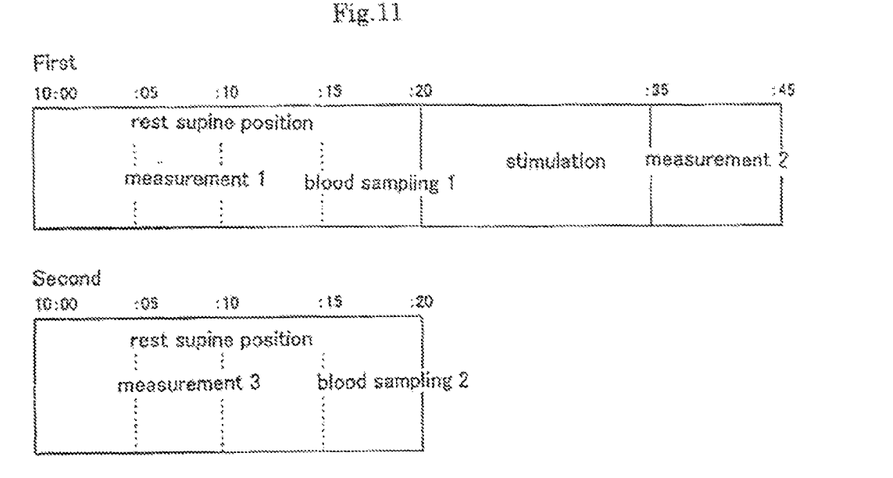
FIG. 11 is a schematic view showing a thermal stimulus protocol to a stimulus part of a sole.

The protocol of a thermal stimulus is shown in FIG. 11. At a resting supine position, an exam of blood pressure etc. and measurement, collection of blood were performed, and then heat stimulus was given thereto. After that, at a resting supine position, exam of blood pressure etc. measurement and collection of blood were performed.

Table 1 shows a result in case where the warm temperature heating stimulus was given to the above-mentioned warm temperature heating stimulus parts by using the warm temperature heating apparatus, and the blood flow volume before and after the stimulus was given to a central part of a wrist joint striation thereof was measured by using the laser Doppler tissue rheometer. From the table, an increase in blood flow volume after application of the stimulus, to that before the stimulus was given, was observed. As shown in this table, when the increase rate of the blood flow was 60% or greater, preferably 120% or more, there were remarkable curative effects.

TABLE 1

| Patient | Blood flow volume before stimulus | Blood flow volume after stimulus | Increase rate |
|---|---|---|---|
| No. 1 | 1.287 | 2.1036 | 63 |
| No. 2 | 3.2791 | 8.0098 | 144 |
| No. 3 | 1.7603 | 2.959 | 68 |
| No. 4 | 2.8101 | 4.6872 | 68 |
| No. 5 | 5.9857 | 13.0065 | 117 |
| No. 6 | 3.453 | 6.9631 | 102 |
| No. 7 | 2.0954 | 4.7401 | 126 |
| No. 8 | 1.4332 | 3.5227 | 146 |
| No. 9 | 1.0091 | 1.7377 | 72 |
| No. 10 | 3.9592 | 8.0699 | 104 |
| No. 11 | 1.5635 | 3.8743 | 148 |

As the blood flow volume increases at the above-mentioned warm temperature heating stimulus parts, the core body temperature rose (+2.1). A decrease in systolic blood pressure (−4.5), an increase in salivary amylase (+34.25), a decrease in cortisol, an improvement of a liver function, a decrease in total cholesterol, a decrease in good and bad cholesterols, a decrease in blood sugar level (−5.25), a decrease in A.I. (arteriosclerosis index) (−0.02), an increase in an Adiponectin, a decrease in leptin were achieved. As a result of measurement of the balance of automatic nerves by a heartrater, stress resistance increased (+12.25).

Therefore, they are parts where while an increase in blood flow volume was achieved in the above-mentioned stimulus application origin parts, the beneficial result such as a rise in core body temperature etc. can be obtained therefrom by the above-mentioned stimulus.

And from time when the increase in blood flow volume or the improvement in increase rate were observed, or at time when it is 60% or greater, preferably 100% or greater, a drug such as a pressor effect agent and a diabetes agent is dosed from a mouth or a drug is stuck on a stimulus application part, so that the drug is supplied to the inside of the body with the stimulus. The dosed drug is effectively conveyed inside the body with the blood flow volume accompanying a stimulus.

Example 2

Figure 12:
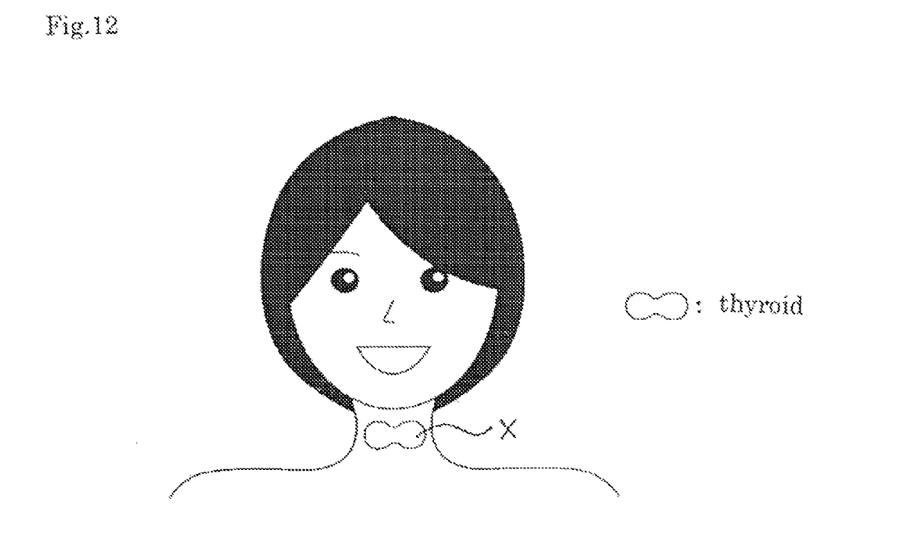
FIG. 12 is a schematic view showing a stimulus part of a part near a thyroid.

In the present embodiment, an acupuncture stimulus was given to part near a thyroid gland, which is a stimulus application origin part (refer to FIG. 12). The thyroid gland is an organ which exists at a shallow position from a body surface, and is observed within a range of 5 mm-30 mm in depth. Therefore, in general, it is examined by using a high frequency surface probe in an ultrasound test. The major axis of the thyroid gland is about 40-50 mm, the thickness diameter thereof is about 12-18 min, the width diameter thereof is about 15-25 mm, and the isthmus-prostate thickness thereof is about 2-4 mm.

Here, ten men and women aged 20 to 60 years old who have diagnosed as high blood pressure were subjects. Expecting an influence on psychological stress which is mediated by autonomic nerves, a disposable acupuncture needle (which was made of stainless steel, 40 mm in length, and 0.18 mm in thickness) was used and inserted to anterior neck region at a depth of 2-3 cm. After keeping the subjects, who were examined, at rest in a state of a dorsal position for 15 minutes, blood pressure, core body temperature, and salivary amylase thereof were measured, and then the acupuncture needle stimulus was applied to them for 15 minutes, and they were measured again immediately after the needle was got out.

The acupuncture needle stimulus was given thereto and the blood flow volume before and after the stimulus was given to a central part of a wrist joint striation thereof was measured by using a laser Doppler tissue rheometer. The measurement result, which is almost the same as that of Table 1 according to the above-mentioned example, was obtained.

As the blood flow volume increases at the above-mentioned warm temperature heating stimulus parts, the core body temperature rises (+2). A decrease in systolic blood pressure (−13), an increase in salivary amylase (−35), a decrease in cortisol (−2.0), an improvement of a liver function, a decrease in total cholesterol (−10.0), a decrease in good and bad cholesterols (−2.0, −6.0), a decrease in blood sugar level (−3.4), a decrease in A.I. (arteriosclerosis index), an increase in an Adiponectin (0.17), a decrease in leptin were achieved.

Therefore, they are parts where while an increase in blood flow volume was achieved in the above-mentioned stimulus application origin parts, where the beneficial result such as a rise in core body temperature etc. can be obtained by the above-mentioned stimulus with the increase in blood flow volume.

And from time when the increase in blood flow volume was observed, a drug such as a pressor effect agent and a diabetes agent was dosed from a mouth or a drug was stuck on a stimulus application part, so that the drug was supplied to the inside of the body with the stimulus. The dosed drug was effectively conveyed inside the body with the blood flow volume accompanying the stimulus.

Example 3

In the present example, a stimulus was given to a part between an outer skin crust and crease side of inner side boundary part of the head of proximal phalanx and the base of 1st proximal phalanx of left and/or right foot.

Figure 13:
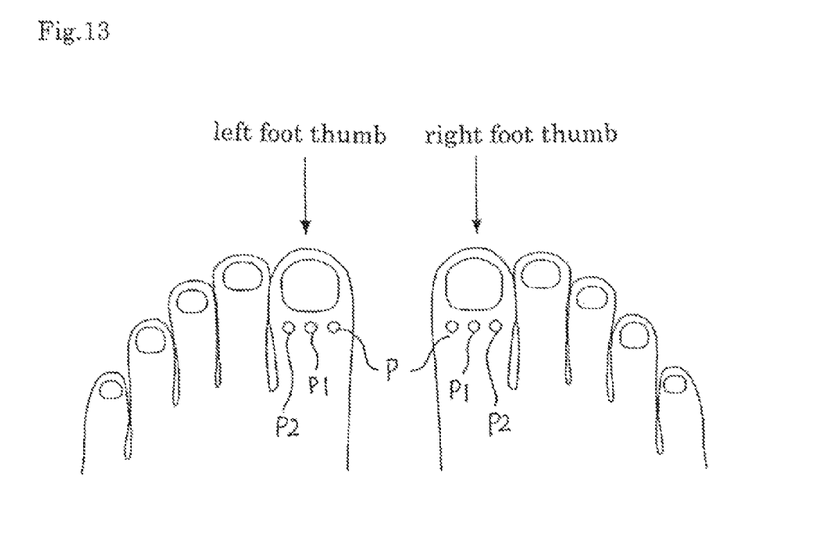
FIG. 13 is a schematic view showing a stimulus part of a hallux of a leg.

FIG. 13 shows first toes wherein a symbol ○ shows the part is a part between an outer skin crust and crease side of inner side boundary part of the head of proximal phalanx and the base of 1st proximal phalanx of left and/or right foot.

Here, ten men and women aged 20 to 60 years old who have diagnosed as diabetes, obesity, and high blood pressure, were subjects. A stimulus was given to the is a part between an outer skin crust and crease side of inner side boundary part of the head of proximal phalanx and the base of 1st proximal phalanx of left and/or right foot.

The moxa cautery was continuously performed five times respectively on left and right parts between an outer skin crust and crease side of inner side boundary part of the head of proximal phalanx and the base of 1st proximal phalanx of left and/or right foot. The quantity of moxa per one moxa cautery is 0.002 g, and the combustion temperature was 80±5 degrees Celsius at maximum. Two sets of treatments, which were performed in the beginning of week and the end of the week, were repeated three times, that is, the treatment was performed six times in total.

The moxibustion stimulus was given thereto and the blood flow volume before and after the stimulus was given to the central part of a wrist joint striation thereof was measured by using a laser Doppler tissue rheometer. The measurement result, which is almost the same as that of Table 1 according to the above-mentioned example, was obtained.

As the blood flow volume increased at the above-mentioned warm temperature heating stimulus parts, and as the blood flow volume increased at the above-mentioned warm temperature heating stimulus parts, a rise in core body temperature (+1.3), a decrease in systolic blood pressure (−13), an increase in salivary amylase (−35), a decrease in cortisol (−2.0), an improvement of a liver function, a decrease in total cholesterol (−10.0), a decrease in good and bad cholesterols (−2.0, −6.0), a decrease in blood sugar level (−3.4), a decrease in A.I. (arteriosclerosis index), an increase in an Adiponectin (0.17), a decrease in leptin were achieved.

Therefore, they are parts where while an increase in blood flow volume is achieved in the above-mentioned stimulus application origin parts and the beneficial result such as a rise in core body temperature etc. can be obtained by the above-mentioned stimulus with the increase in blood flow volume.

And from time when the increase in blood flow volume is observed, a drug such as a pressor effect agent and a diabetes agent was dosed from a mouth or a drug was stuck on a stimulus application part, so that the drug was supplied to the inside of the body with the stimulus. The dosed drug was effectively conveyed inside the body with the blood flow volume accompanying a stimulus.

INDUSTRIAL APPLICABILITY

Treatment for releasing stress, treatment of high blood pressure, diabetes, etc., drug administration, and drug conveyance by drug administration, drug.

The invention claimed is:

1. A drug supply start timing determination method comprising the following steps of:
applying a stimulus to a stimulus application origin part of a body surface by a stimulus applying apparatus, the stimulus application origin part being in right or left foot sole at least one part selected from the group consisting of a part of os metatarsale primam 1 and 2 interossous; a part of os metatarsale primam 2 and 3 interossous, and a part that intersects a perpendicular line of a medial malleolus on an extension line of a medial margin on os metatarsale primam 1 and 2 interossous,
measuring a blood flow volume by a laser Doppler tissue rheometer which is attached to an inner and central part of a wrist joint, and
determining a drug supply timing by regarding an increase in the blood flow volume after application of the stimulus to that before the application thereof, as an index of a drug supply start timing.

2. The drug supply start timing determination method according to claim 1, wherein the drug supply timing is time when an increase rate of the blood flow volume measured by the laser Doppler tissue rheometer is 60% or greater to a measured rate of the blood flow volume before the application of the stimulus.

3. The drug supply start timing determination method according to claim 1, wherein the stimulus is non-simultaneously and independently applied to at least two parts selected from said stimulus application origin parts.

4. A method of supplying a drug to a body, comprising the following steps of:
  determining the drug supply timing according to the drug supply start timing determination method of claim 1, and
  supplying the drug to an inside of the body when the blood flow volume is increased with the stimulus according to the method of claim 1.

* * * * *